US007425322B2

(12) United States Patent
Cohn et al.

(10) Patent No.: US 7,425,322 B2
(45) Date of Patent: Sep. 16, 2008

(54) RESPONSIVE BIOMEDICAL COMPOSITES

(75) Inventors: Daniel Cohn, Jerusalem (IL); Alejandro Sosnik, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 172 days.

(21) Appl. No.: 10/951,036

(22) Filed: Sep. 24, 2004

(65) Prior Publication Data

US 2005/0165128 A1 Jul. 28, 2005

Related U.S. Application Data

(63) Continuation of application No. PCT/IL03/00238, filed on Mar. 19, 2003.

(51) Int. Cl.
 *A61K 31/74* (2006.01)

(52) U.S. Cl. .............. 424/78.02; 424/78.03; 424/78.18; 424/400; 424/401; 424/443; 424/450; 424/486; 424/487; 424/489; 524/504; 524/505; 525/79; 525/90; 525/93; 525/941

(58) Field of Classification Search .............. 424/78.02, 424/78.03, 78.18, 400, 401, 443, 450, 486, 424/487, 489; 524/504, 505; 525/79, 90, 525/93, 941
See application file for complete search history.

(56) References Cited

U.S. PATENT DOCUMENTS

| 4,188,373 | A | 2/1980 | Krezanoski |
| 4,938,763 | A | 7/1990 | Dunn et al. |
| 5,204,382 | A | 4/1993 | Wallace et al. |
| 5,252,318 | A | 10/1993 | Joshi et al. |
| 5,403,893 | A | 4/1995 | Tanaka et al. |
| 5,410,016 | A | 4/1995 | Hubbell et al. |
| 5,711,958 | A | 1/1998 | Cohn et al. |
| 5,766,704 | A | 6/1998 | Allen et al. |
| 5,824,333 | A | 10/1998 | Scopelianos et al. |
| 5,939,485 | A | 8/1999 | Bromberg et al. |
| 6,001,394 | A | 12/1999 | Daculsi et al. |
| 6,004,573 | A | 12/1999 | Rathi et al. |
| 6,136,333 | A | 10/2000 | Cohn et al. |
| 6,201,065 | B1 | 3/2001 | Pathak et al. |
| 6,271,278 | B1 | 8/2001 | Park et al. |
| 6,309,659 | B1 | 10/2001 | Clokie |
| 6,316,011 | B1 | 11/2001 | Ron et al. |
| 6,417,247 | B1 | 7/2002 | Armstrong et al. |

FOREIGN PATENT DOCUMENTS

| WO | WO 97/00275 | 1/1997 |
| WO | WO 97/05185 | 2/1997 |
| WO | WO 98/06438 | 2/1998 |
| WO | WO 98/29487 | 7/1998 |

OTHER PUBLICATIONS

Jeong et al., Nature 388, 860 (1997).
Hutmacher, Biomaterials 21, 2529 (2000).
Hoffman A.S. et al., J. Biomed. Mater. Res. 24,21 (1990).
Gurrny R., Polymer Biomaterials in Solution, as Interfaces and as Solids, p. 683, S.L. Cooper, C.H. Bamford and T. Tsuruta (Editors), VSP-Utrecht, The Netherlands (1995).
Gopferich A., Biomaterials 17, 103 (1996).
Esposito et al., Int. J. Pharm. 142, 9 (1996).
Cohn et al., Polymer 28, 2018 (1987).
Cohn et al., J. Biomed. Mater. Res. 59, 273 (2002).
Cohn D. et al, Biomed. Mater. Res. 21, 1301 (1987).
Alexandridis et al., Colloids and Surfaces A, 96, 1 (1995).
Vert et al., Polym. Int. 45, 419 (1998).
Tormala P. et al., Biomaterials 16, 1353 (1995).
Sawhney S.A. et al., J. Biomed. Mater. Res. 24, 1397 (1990).
Ramakrishna S. et al., Composites Science and Technology 61, 1189 (2001).
Mikos et al., Biomaterials 21, 2405 (2000).
Lee et al., J. Control. Release 73 315 (2001).
Langer, R., J. Biomed. Mat. Res. 28, 1465 (1994).
Langer et al., Biomaterials 21, 259 (2000).
Kost et al., J.Biomed. Mater. Res. 50, 388 (2000).
Kissel T. et al., J. Biomed. Mater. Res. 30, 31 (1996).

*Primary Examiner*—Bernard Lipman
(74) *Attorney, Agent, or Firm*—Martin Fleit; Paul D. Bianco; Fleit Gibbons Gutman Bongini & Bianco PL

(57) ABSTRACT

A responsive polymeric system including a responsive polymeric component capable of undergoing a transition that results in a sharp increase in viscosity in response to a triggering effected at a predetermined body site. The system includes a solid non-ceramic reinforcing component which reinforces the polymeric component, and an aqueous-based solvent wherein the viscosity of the responsive polymeric component increases by at least about 2 times upon exposure to a predetermined trigger.

28 Claims, 1 Drawing Sheet

RESPONSIVE BIOMEDICAL COMPOSITES

RELATED APPLICATION

This application is a continuation of International Application No. PCT/IL03/00238, filed Mar. 19, 2003, the contents of which are here incorporated by reference in their entirety. Applicants claim the benefit of 35 USC Sec. 120.

BACKGROUND OF THE INVENTION

1. Field of the Invention

The present invention relates to a reinforced responsive polymeric system. More specifically, the present invention relates to a polymeric system comprising at least two phases, an environmentally responsive polymeric component and a solid reinforcing component, which is introducible into the body and which undergoes a change in viscosity at a predetermined body site, said polymeric system being useful in drug delivery, tissue engineering, gene therapy and other biomedical applications.

2. Prior Art

There is a wide variety of materials which are foreign to the human body and which are used in direct contact with its organs, tissues and fluids. These materials are called Biomaterials, and they include, among others, polymers, ceramics, biological materials, metals, composite materials and combinations thereof.

The development of polymers suitable to be implanted without requiring a surgical procedure, usually named injectable polymers, has triggered much attention in recent years. These materials combine low viscosity at the injection stage, with a gel or solid consistency developed in situ, later on. The systems of the present invention are preferably used, without limitation, as matrices for the controlled release of biologically active agents, as sealants, as coatings and as barriers in the body. The area of Tissue Engineering represents an additional important field of application of the reinforced responsive systems disclosed hereby, where they can perform as the matrix for cell growth and tissue scaffolding.

The syringeability of injectable biomedical systems is their most essential advantage, since it allows their introduction into the body using minimally invasive techniques. Furthermore, their low viscosity and substantial flowability at the insertion time, enable them to reach and fill spaces, otherwise inaccessible, as well as to achieve enhanced attachment and improved conformability to the tissues at the implantation site. On the other hand, the sharp increase in viscosity is a fundamental requirement for these materials to be able to fulfill any physical or mechanical function, such as sealing or performing as a barrier between tissue planes. The high viscosities attained play also a critical role in generating syringable materials that, once at the implantation site, are also able to control the rate of release of drugs or can function as the matrix for cell growth and tissue scaffolding. Clearly, biodegradability is yet another important requirement for some of these materials.

A polymer network is characterized by the positive molecular interactions existing between the different components of the system. These inter-reactions may be physical in nature, such as chain entanglements, or chemical such as ionic interactions, hydrogen bonding, Van der Waals attractions and covalent bonding. Bromberg et al. (U.S. Pat. No. 5,939,485) developed responsive polymer networks exhibiting the property of reversible gelation triggered by a change in diverse environmental stimuli, such as temperature, pH and ionic strength. Pathak et al. (U.S. Pat. No. 6,201,065) disclosed thermo-responsive macromers based on cross-linkable polyols, such as PEO-PPO-PEO triblocks, capable of gelling in an aqueous solution. The macromers can be covalently crosslinked to form a gel on a tissue surface in vivo. The gels are useful in a variety of medical applications including drug delivery.

Park et al. (U.S. Pat. No. 6,271,278) developed superporous hydrogel composites formed by polymerizing one or more ethylenically-unsaturated monomers, and a multi-olefinic cross-linking agent, in the presence of particles of a disintegrant and a blowing agent.

The term "thermosensitive" refers to the capability of a polymeric system to achieve significant chemical, mechanical or physical changes due to small temperature differentials. The resulting change is based on different mechanisms such as ionization and entropy gain due to water molecules release, among others (Alexandridis and Hatton, Colloids and Surfaces A, 96, 1 (1995)). Since one of their fundamental advantages is to avoid the need for an open surgical procedure, thermo-responsive materials are required to be easily syringable, combining low viscosity at the injection stage, with a gel or solid consistency being developed later on, in situ.

Thermosensitive gels can be classified into two categories: (a) if they have an upper critical solution temperature (UCST), they are named positive-sensitive hydrogels and they contract upon cooling below the UCST, or (b) if they have a lower critical solution temperature (LCST), the are called negative-sensitive hydrogels and they contract upon heating above this temperature.

The reverse thermo-responsive phenomenon is usually known as Reversed Thermal Gelation (RTG) and it constitutes one of the most promising strategies for the development of injectable systems. The water solutions of these materials display low viscosity at ambient temperature, and exhibit a sharp viscosity increase as temperature rises within a very narrow temperature interval, producing a semi-solid gel once they reach body temperature. There are several RTG displaying polymers. Among them, poly(N-isopropyl acrylamide) (PNIPAAm) (Tanaka and co-workers in U.S. Pat. No. 5,403,893 and Hoffman A. S. et al., J. Biomed. Mater. Res., 24, 21 (1990)), PEG-PLGA-PEG triblock polymers (Jeong et al., Nature, 388, 860 (1997)), etc. Unfortunately, poly(N-isopropyl acrylamide) is non-degradable and, in consequence, is not suitable for a diversity of applications where biodegradability is required.

Definitely one of the most important RTG-displaying materials is the family of poly(ethylene oxide)/poly(propylene oxide)/poly(ethylene oxide) (PEO-PPO-PEO) triblocks, available commercially as Pluronic$^{RTM}$ (Krezanoski in U.S. Pat. No. 4,188,373). Adjusting the concentration of the polymer, renders the solution with the desired liquid-gel transition. However, relatively high concentrations of the triblock are required (typically above 15-20%) are required to produce compositions that exhibit such a transition, even minor, at commercially or physiologically useful temperatures. Another known system which is liquid at room temperature, and becomes a semi-solid when warmed to about body temperature, is disclosed in U.S. Pat. No. 5,252,318, and consists of tetrafunctional block polymers of polyoxyethylene and polyoxypropylene condensed with ethylenediamine (commercially available as Tetronic.$^{RTM}$).

The endothermic phase transition taking place, is driven by the entropy gain caused by the release of water molecules bound to the hydrophobic groups in the polymer backbone. Unfortunately, despite of their potential, some fundamental aspects of their performance severely restrict their clinical use. Even though these materials exhibit a significant increase in viscosity when heated up to 37° C., the levels of viscosity attained are not high enough for most clinical applications. Derived from this fundamental limitation, these systems display unsatisfactory mechanical properties and unacceptably short residence times at the implantation site. Furthermore, due to these characteristics, these gels have high permeabilities, a property which renders them unsuitable for drug delivery applications because of the fast drug release kinetics of these gels. Despite of their clinical potential, these materials have failed to be used successfully in the clinic, because of serious performance limitations (Esposito et al., Int. J. Pharm. 142, 9 (1996)).

Composite Materials comprising a matrix and a reinforcing component have recently attracted much attention as new materials for improved biomedical devices. Usually used reinforcing components are polymeric or ceramic materials, as well as metals, carbons (mainly fibers), and biological materials. The reinforcement may be in a fibrous or particulate form, or creating specific three dimensional constructs. Examples of the latter are amorphous lattice structures, meshes and fab, non-woven structures, a filament wound or braided structures, or honeycomb structures. Also, the reinforcing constituent may be a macro, micro or nano-sized material and it may be hollow, porous or solid.

Whereas the vast majority of the biomedical composites are stiff structures, engineered to perform in conjunction with hard tissues, work has also been conducted aiming at developing composite materials for soft tissue implants, such as arterial prostheses, pericardial and hernial patches and tracheal conduits. So far, the major uses of biomedical composites have been in reconstructive surgery for joint replacement, as ligaments and tendons and as a variety of fixation devices. While the matrix is generally a polymer, typically, devices comprised carbon and glass fibers. Further examples of the expanding use of composite materials in diverse orthopaedic and reconstructive applications are glass fibre polyurethane splints and porous PTFE-carbon fiber patches and composites in maxillofacial and skull defect reconstruction. Additional novedous uses, such as intramedular nails and ureter prosthesis are described by S. Ramakrishna et al. (Composites Science and Technology, 61, 1189 (2001)).

The biocompatibility of the prosthesis is a necessary but by no means sufficient condition for a successful implant action. The healing and remodeling of the natural tissue and the successful incorporation of the implant are greatly affected by the stress field induced on the tissue. Because the mechanical properties of the implant have a determining effect on these phenomena, the importance of implants that mimic the mechanical response of the replaced tissue becomes apparent. The main characteristics of this response will vary significantly with the type of tissue, e.g. osseous calcified versus soft connective.

Anisotropy, an inherent merit of fibrous composite materials, is an important characteristic common to most biological tissues. For example, blood vessels are complex, multilayered structures, comprising collagen and elastin fibers, smooth muscle cells, ground substance and endothelium. The anisotropy of blood vessels is because of the orientation of their fibrous components. An additional important characteristic shared by most natural fibrous soft tissues pertains to their non-Hookean dimensional response under physiological loading modes, where J-shaped stress-strain curves are exhibited.

Biodegradability plays a unique role in a diversity of devices, implants and prostheses, being this property an additional important requirement for some of these materials. Their most obvious advantage pertains to the fact that there is no need to remove the system, once it has accomplished its objectives. In addition, they can perform as matrices for the release of bioactive molecules and result in improved healing and tissue regeneration processes. Biodegradable polymers such as polyesters of $\alpha$-hydroxy acids, like lactic acid or glycolic acid, are used in diverse applications such as bioabsorbable surgical sutures and staples, some orthopedic and dental devices, drug delivery systems and more advanced applications such as the absorbable component of selectively biodegradable vascular grafts, or as the temporary scaffold for tissue engineering. The synthesis and biodegradability of poly(lactic acid) was reported by several groups (Tormala P. and group, Biomaterials, 16, 1353 (1995) and Gopferich A., Biomaterials, 17, 103 (1996)). Biodegradable polyanhydrides (Langer, R., J. Biomed. Mat. Res., 28, 1465 (1994)) and polyorthoesters (Gurny R., 'Polymer Biomaterials in Solution, as Interfaces and as Solids', Page 683, S. L. Cooper, C. H. Bamford and T. Tsuruta (Editors), VSP-Utrecht, The Netherlands (1995)) having labile backbone linkages, have been developed, the disclosures of which are incorporated herein. Polymers which degrade into naturally occurring materials, such as polyaminoacids, also have been synthesized. Degradable polymers formed by copolymerization of lactide, glycolide, and $\epsilon$-caprolactone have been disclosed (Kissel T. and collaborators, J. Biomed. Mater. Res., 30, 31-40 (1996). Polyether-polyester combinations especially of polyethylene glycol (PEG) and aliphatic polyesters like poly(lactic acid), poly(glycolic acid) and poly(caprolactone), either as a blend or as a copolymer, in order to increase the hydrophilicity and degradation rate, have been reported. Most of the work was focused on poly(ethylene glycol)/poly(glycolic) (PEG-PGA) or poly(lactic) (PEG-PLA) acid materials (Cohn et al., Polymer, 28, 2018-2022 (1987) and J. Biomed. Mater. Res., 21, 1301-1316 (1987) and Sawhney S. A. and Hubbell J. A., J. Biomed. Mater. Res. 24, 1397 (1990)). Furthermore, these polymers present relatively fast degradation rates, from a few days to a few months. This drawback constitutes one of the relevant application limitations. Another group of poly(ether-ester)s is the poly(ethylene glycol)-poly (caprolactone) (PEG-PCL)-based polymers. Thus, a broad work was done on high MW PEG-PCL block copolymers. Vert and co-workers (Polym. Int., 45, 419 (1998) synthesized and characterized PEG-PCL copolymers of intermediate molar masses with both PEG and PCL crystallizable blocks, using dicyclohexylcarbodiimide as coupling agent. Findings of cytotoxicity and hemocompatibility tests showed biocompatibility. Lee and partners (J. Control. Release, 73, 315 (2001) reported amphiphilic block copolymeric micellar systems composed of methoxy poly(ethylene glycol)/epsilon-caprolactone for DDS. Cohn et al (J. Biomed. Mater. Res. 59, 273 (2002) produced series of PEG-PCL-containing biodegradable poly(ether-ester-urethane)s, covering a wide range of compositions. Finally, reduction of adhesions associated with post-operative surgery based on the administration of polymeric composition comprising chain-extended poly(hydroxy-carboxylic acid)/poly(oxyalkylene) ABA triblocks to a site in the body which has been subjected to trauma, e.g. by surgery, excision or inflammatory disease was described (Cohn et al. in U.S. Pat. Nos. 5,711,958 and 6,136,333).

Unfortunately, the few absorbable polymers clinically available today are hydrophobic solids which are, therefore, clearly unsuitable for non-invasive surgical procedures, where injectability is a fundamental requirement. The only way to avoid the surgical procedure with these polymers, is to inject them as micro or nanoparticles or capsules, typically containing a drug to be released. As an example, injectable implants comprising calcium phosphate particles in aqueous viscous polymeric gels, were first proposed by Wallace et al. in U.S. Pat. No. 5,204,382. Even though these the ceramic component is generally considered to be nontoxic, the use of nonabsorbable particulate material seems to trigger a foreign body response both at the site of implantation as well as at remote sites, due to the migration of the particles, over time.

Among the approaches developed, the in situ precipitation technique developed by R. Dunn, as disclosed in U.S. Pat. No. 4,938,763, is one strategy worth mentioning. These systems comprise a water soluble organic solvent, in which the polymer is soluble. Once the system is injected, the organic solvent gradually dissolves in the aqueous biological medium, leaving behind an increasingly concentrated polymer solution, until the polymer precipitates, generating the solid implant in situ. A similar approach has been reported by Kost et al (J. Biomed. Mater. Res., 50, 388 (2000)).

In situ polymerization and/or cross-linking is another important technique used to generate injectable polymeric systems. Hubbell et al described in U.S. Pat. No. 5,410,016, water soluble low molecular precursors having at least two polymerizable groups, that are syringed into the site and then polymerized and/or crosslinked in situ chemically or preferably by exposing the system to UV or visible radiation. Mikos et al (Biomaterials, 21, 2405 (2000)) described similar systems, whereas Langer et al (Biomaterials, 21, 259 (2000)) developed injectable polymeric systems based on the percutaneous polymerization of precursors, using UV radiation. An additional approach was disclosed by Scopelianos and coworkers in U.S. Pat. No. 5,824,333 based on the injection of hydrophobic bioabsorbable liquid copolymers, suitable for use in soft tissue repair.

Unfortunately, all these techniques have serious drawbacks and limitations, which significantly restrict their applicability. The paradox in this area has to do, therefore, with the large gap existing between the steadily increasing clinical demand for Injectables, on one hand, and the paucity of materials suitable to address that need, on the other hand.

The emerging field of Tissue Engineering and its nascent clinical application, represents a major breakthrough both conceptually as well as technologically. The objective of Tissue Engineering is to induce regeneration of functional tissue, by providing the appropriate three-dimensional scaffolding construct on which cells will be able to grow, differentiate and generate new tissue. Tissue Engineering systems comprise a matrix containing the cells and a scaffold which functions as a substrate for cells attachment. Customarily, the matrix consists of natural or synthetic hydrogels such as alginates, hyaluronic acid, collagen gels and additional materials such as fibroin. On the other hand, the scaffolds typically comprise biodegradable aliphatic polyesters, such as polylactic acid, polyglycolic acid and polycaprolactone and copolymers (Hutmacher, Biomaterials, 21, 2529-2543 (2000)). Clearly, the composition and mechanical properties of the materials, strongly affect the ability of the system to actively promote the regeneration of autologous functional tissue. In addition, the macrostructural characteristics of the scaffold, play also a fundamental role in determining the type of cells and tissue components present in the new tissue. The template's ultimate task is to provide a gradually disappearing, temporary construct for the generation of viable new tissue. Therefore, if autologous tissue is to regenerate and replace the construct, biodegradability is one of its indispensable attributes. It is also necessary for the template to perform as an adhesive substrate for cells, promoting their growth and differentiation, while retaining cell function. Also, for a scaffold to perform successfully, it is required to be biocompatible, to display the right porosity and to be mechanically suitable.

In general terms, Tissue Engineering can be classified into in vitro and in vivo types. While the former concentrates on the ex vivo generation of tissues from cells removed from a donor site, the latter aims at regenerating functional tissue at the site of implantation, by the combined action of biomolecules and cells, in situ.

SUMMARY OF THE INVENTION

A variety of techniques were used to manufacture three-dimensional polymeric scaffolds, including solvent casting/solvent leaching, gas foaming, phase separation, three-dimensional printing and the use of various types of preformed constructs.

The fundamental advantage of RTG-displaying matrices in Tissue Engineering derives from the viscosity differential inherent to their reverse thermo-responsive nature. This will enable their incorporation into the scaffolding structure or their injection into the body, as very low viscosity water solutions. It is only when the temperature of the system rises above its $T_t$, at the site of implantation, that the viscosity will increase sharply and the matrix will gel. This will allow both the incorporation of the cells into the scaffolding construct as well as their delivery directly to the tissue, in a gentle and controlled way. The various parameters of the gel, most importantly $T_t$ and the viscosity of the gel at 37° C., can be easily fine tuned. i) Within this novel conceptual framework, the present invention discloses also RTG-based composite materials in Tissue Engineering. This can be illustrated, for example, and without limitation, by in vivo-generated tubular structures that will perform in various areas such as the vascular and urological fields. The present invention also discloses multi-layered constructs which perform as templates for in vivo co-culturing of different types of cells, most importantly endothelial cells and smooth muscle cells. The present invention also discloses constructs which perform as templates for in vivo co-culturing of different types of cells, most importantly endothelial cells and smooth muscle cells. Multi-component systems, most importantly consisting of two components where one generates the matrix while the other produces the scaffolding structure, are also disclosed hereby. Clearly, each of the constituents is characterized by distinct chemical and physical properties so that their final rheological properties and spatial distribution support their performance as the matrix and the scaffold, respectively.

According to the present invention there is now provided a responsive polymeric system, comprising a responsive polymeric component capable of undergoing a transition that results in a sharp increase in response to a triggering effected at a predetermined body site; a solid non-ceramic reinforcing component which reinforces the responsive polymeric component at said predetermined body site and an aqueous-based solvent, wherein the viscosity of said responsive polymeric component increases by at least about 2 times upon exposure to a predetermined trigger.

DETAILED DESCRIPTION OF PREFERRED EMBODIMENTS OF THE INVENTION

Figure 1:
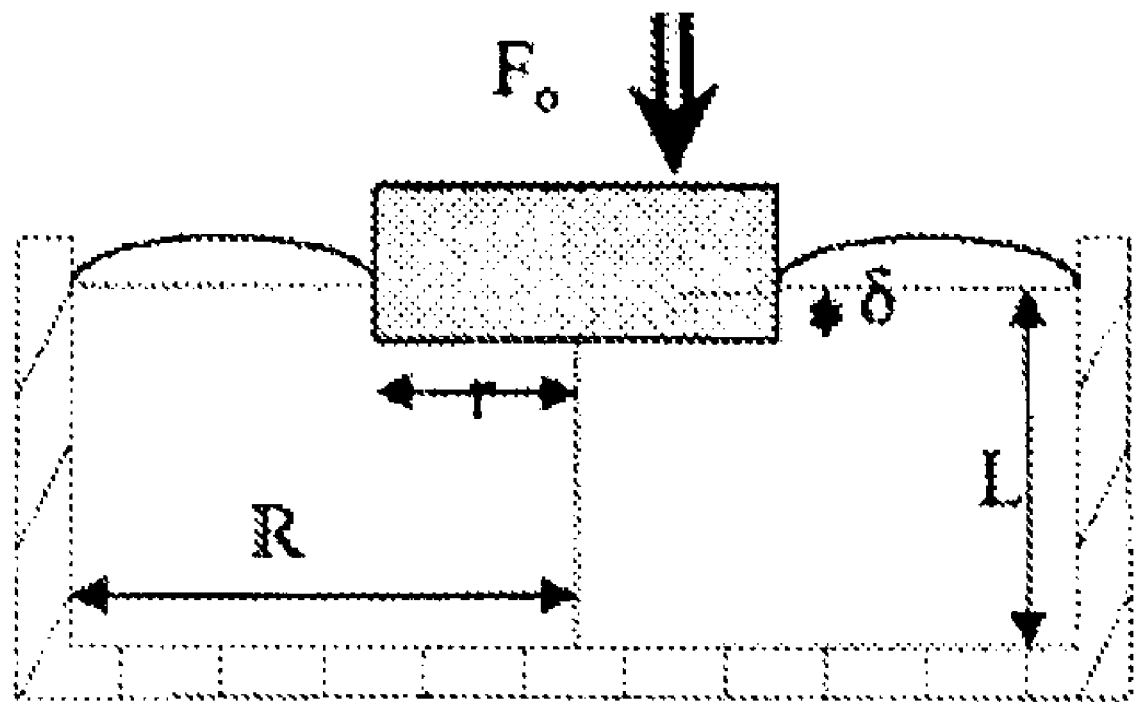
FIG. 1 is a schematic illustration of compression test.

In especially preferred embodiments of the present invention said solid reinforcing component is a polymeric reinforcing component.

In WO 98/06438 there is described a pharmaceutical composition comprising a reversed thermally viscosifying polymer network. The polymer network includes at least one responsive polymer component and at least one structural component.

WO 98/29487 and WO 97/00275 disclose responsive polymer networks exhibiting the property of reversible gelation.

U.S. Pat. No. 6,316,011 discloses a reverse thermally viscosifying composition.

U.S. Pat. No. 6,309,659 discloses a reverse phase connective tissue repair composition comprising demineralized bone powder and a reverse phase mixture of Poloxamer and water.

U.S. Pat. No. 6,004,573 discloses an aqueous biodegradable polymeric drug delivery composition having reverse thermal gelation properties.

U.S. Pat. No. 6,417,247 discloses polymer/ceramic composites. Calcium phosphate ceramics are preferred for use as the ceramic component of implants in the repair of bone defects because these materials are non-toxic, non-immunogenic, and are composed of calcium and phosphate ions, the main constituents of bone. Calcium phosphate implants may be osteoconductive and have the apparent ability to become directly bonded to bone. However, the mechanical properties of calcium phosphate ceramics make them ill suited to serve as a structural element. For this reason the ceramic components is combined with a polymeric component which adds elastic strength to the composition overcoming the shortcomings of the ceramic alone while retaining its positive features. The polymeric components are preferably polysaccharides, polyamides or polyaminoacids and add elastic strength to the system.

U.S. Pat. No. 6,001,394 discloses a biomaterial composition comprising an inorganic phase and a liquid phase including an aqueous solution of a water-soluble, biocompatible polymer, which is self-crosslinkable under the effect of the pH of the medium.

U.S. Pat. No. 5,939,485 discussed above discloses a responsive component capable of aggregation in response to a change in an environmental stimulus, and a structural component which supports and interacts with the responsive component, however the structural component as disclosed in said patent are described as being dissolved in an aqueous-based solvent and therefore said structural component is not a solid.

As will be noted note of said patents teach or suggest the responsive polymeric system having the components and the properties as described herein.

In a preferred embodiment of the present invention said predetermined trigger is temperature, wherein said responsive polymeric system undergoes said increase in viscosity when being heated up, preferably from a lower temperature to body temperature and more preferably from room temperature to body temperature.

Preferably said responsive polymeric component is biodegradable.

In preferred embodiments of the present invention said responsive polymeric component is polymerizable and/or crosslinkable in situ, by means selected from a group consisting of specific chemical compounds added to the system, heat, ionic strength, pH or radiative energy and combinations thereof, said polymerization and/or cross-linking bond being selected from a group consisting of covalent, secondary or ionic bonds, physical interactions and combinations thereof.

In said embodiments preferably said polymerization and/or cross-linking is temporary so that the system is able to essentially revert in situ, to an unpolymerized and/or non-crosslinked state.

In especially preferred embodiments of the present invention said responsive component is selected from a group consisting of a polyoxyalkylene polymer, a block copolymer comprising polyethylene oxide (PEO) and polypropylene oxide (PPO) selected from a group consisting of a diblock, a triblock or a multiblock, a segmented block copolymer comprising polyethylene oxide (PEO) and polypropylene oxide (PPO) chains, wherein said PEO and PPO chains are connected via a chain extender, a poly(alkyl-co-oxyalkylene) copolymer having the formula R—(OCH$_2$CH)$_n$—OH, where R is an hydrophobic group, a poly(N-alkyl substituted acrylamide), cellulose and cellulose derivatives and combinations thereof.

Of the above preferably said responsive component is a polyoxyalkylene polymer having terminal moieties selected from a group consisting of hydroxyl, carboxyl, thiol, amine, isocyanate, or double bond-containing active groups and combinations thereof.

In said embodiments said responsive component is preferably biodegradable.

In further preferred embodiments of the present invention said responsive component is a segmented block copolymer comprising polyethylene oxide (PEO) and polypropylene oxide (PPO) chains, wherein said PEO and PPO chains are connected via a chain extender, wherein said chain extender is selected from a group consisting of phosgene, aliphatic or aromatic dicarboxylic acids or their reactive derivatives such as acyl chlorides and anhydrides or other molecules able to react with the OH terminal groups of the PEO and PPO chains, such as dicyclohexylcarbodiimide (DCC), aliphatic or aromatic diisocyanates such as hexamethylene diisocyanate (HDI) or methylene bisphenyldiisocyanate (MDI) or cyanuric chloride or any other bifunctional or multifunctional segment, and combinations thereof.

Preferably said poly(N-alkyl substituted acrylamide) is poly(N-isopropyl acrylamide).

As indicated hereinbefore, preferably said responsive component contains a molecule/s, to be delivered into the body.

Preferably said responsive component contains living cells such as endothelial cells, hepatocytes, astrocytes, myocytes, osteoblasts, chondrocytes and/or combinations thereof.

In especially preferred embodiments said initially of the present invention said responsive component serves as matrix for cell differentiation and growth in the field of Tissue Engineering.

In most preferred embodiments of the present invention said solid reinforcing component is a macro, micro or nano-sized material selected from the group consisting of a polymer, a metal, a carbon, a biological material, and combinations thereof, wherein said solid reinforcing component is selected from the group consisting of a particle, a sphere, a capsule, a rod, a slab, a fiber, a mesh, a fabric, a ribbon, a non-woven structure, a filament wound structure, a honeycomb structure or a braided structure, and combinations thereof, wherein said solid reinforcing component is hollow, porous or solid, and combinations thereof.

In most preferred embodiments of the present invention said solid reinforcing component is a polymer selected from a group consisting of polycarbonates, polyurethanes, polyamides, polyesters, polyanhydrides, polypeptides, polysaccharides, polyolefins, acrylic and methacrylic polymers, silicone polymers and blends, semi-IPNs, IPNs, copolymers and combinations thereof.

In most preferred embodiments of the present invention said solid reinforcing component is introduced as a non-viscous oligomer containing reactive moities such as, and without limitation, double bonds, and reacted in situ to generate the solid reinforcement at a predetermined body site.

In most preferred embodiments of the present invention said solid reinforcing component is introduced as a water soluble monomer, oligomer or polymer such as poly(ethylene glycol) chains or any water soluble PEO-containing copolymer such as, and without limitation, PEO-PPO-PEO, PPO-PEO-PPO, PTMO-PEO-PTMO, PLA-PEO-PLA, PEO-PLA-PEO, PCL-PEO-PCL, PEO-PCL-PEO or any other telechelic water soluble oligomers or polymers containing segments such as, and without limitation, vinyl alcohol, acrylic acid, methacrylic acid, acrylamide, N-vinyl pyrrolidone, oligo or polysaccharides, amino acids, oligopeptides, peptides or proteins comprising double bond reactive groups such as acrylates or methacrylates or any other group able to react in a predetermined body site, and said water soluble molecule is reacted in situ to generate the solid reinforcement.

It is an additional object of the invention to partially or totally polymerize and/or crosslink one or more components of the system, before, during or after implantation time. In addition, the partial or total polymerization and/or crosslinking of one or more components of the system can be carried out by diverse techniques such as, without limitation, chemical systems (e.g initiator/catalyst), radiation triggered (e.g. UV/Visible light radiation, laser radiation), and combinations thereof.

It is a more preferred object of the invention components of the invention to segregate over time due to their chemical incompatibility and/or due to a polymerization and/or crosslinking reaction.

It is an even more preferred object of the components of the invention to form initially a homogeneous macroscopic system and, over time, at least two macro, micro or nanoscopic, continuous or discontinuous phases are formed, creating independent or interconnected domains within the system, having several geometries, architectures and spatial arrays, dispersed homogeneously or heterogeneously, isotropically or anisotropically.

Preferably said solid reinforcing component is a biodegradable material.

Preferably, said solid reinforcing component is of tissular source.

In other preferred embodiments said solid reinforcing component is selected from a group consisting of elastin, a collagenous material, albumin, a fibrinous material, demineralized tissue or an acellular tissue matrix and combinations thereof.

Preferably said solid reinforcing component contains a biomolecule/s, to be delivered into the body.

In preferred embodiments of the present invention said solid reinforcing component serves as scaffold for cell differentiation and growth in the field of Tissue Engineering.

In preferred embodiments of the present invention said solid reinforcing component is chemically or physically bound to the matrix, before and/or during and/or after injection.

The novel, tailor-made compositions of the present invention display advantageous properties unattainable by the prior art by capitalizing, in a unique and advantageous way, on the Reverse Thermal Gelation phenomenon and the superior mechanical properties inherent to reinforced Composite Materials.

Compositions according to this invention are suitable to be used in the human body, preferably in applications where the combination of ease of insertion and enhanced initial flowability, on one hand, and post-implantation high viscosity and superior mechanical properties, on the other hand, are required.

Aiming to expand the clinical applicability of the biomedical hydrogels, it is an object of this invention to provide reinforced responsive polymeric systems: new hydrogel biocomposites. These materials will find a variety of important biomedical applications in the biomedical field, such as in non-invasive surgical procedures, in drug delivery systems, in the prevention of post-surgical adhesions and in the Tissue Engineering field, designed to cover a broad range of mechanical properties. In the case of biodegradable systems, these materials are engineered to display different degradation kinetics. This was achieved by combining polymers displaying Reverse Thermal Gelation (RTG) behavior (the matrix of the composite) and a solid reinforcement.

It is an additional object of the invention to introduce hydrolytically unstable segments along the polymeric backbone, allowing, therefore, to fine tune both the degradation rate of the polymer molecule as well as control the stability of the whole system and its rheological properties.

It is an additional object of the invention to render these compositions with specific biological functions by incorporating biomolecules of various types, physically (by blending them into the system) or chemically (by covalently binding them to the polymer).

It is an additional object of the invention to incorporate cells of various types into these materials for cell differentiation and growth, where said RTG-displaying polymers perform as the matrix and said resulting solid reinforcement performs as the scaffold.

Within this novel conceptual framework, the present invention also discloses new biomedical systems. This can be illustrated, for example, by (i) in vivo-generated tubular structures that will perform in various areas such as the vascular and urological fields and (ii) templates for co-culturing of different types of cells, such as, and without limitation, endothelial cells and smooth muscle cells, such as multilayered constructs or structures comprising areas that display different properties. These biomedical composites, most importantly consisting of two constituents where one generates the matrix while the other produces the scaffolding structure, are also disclosed hereby. Clearly, each of the components is characterized by distinct chemical and physical properties so that their final Theological properties and spatial distribution support their performance as the matrix and the scaffold, respectively.

The term "different reverse thermal gelation behavior" as used herein is intended to denote inter alias that the different components attain different viscosities at 37° C., that they have different Ti values, meaning that their viscosities raise at different temperatures, that one may have to dissolve over time before it starts to be RTG relevant, and meaning that at least one can polymerize and/or crosslink as opposed to other or others.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Pluronic F-127 Gel in Water (20% w/w), Reinforced with Glass Fibers 3 g of F-127 were dissolved in 12 g water at around 5° C. temperature, generating a 20% w/w solution. While at this temperature (below F-127's gelling temperature), 1.2 g of glass fibers were added to the solution. The system was then heated at 37° C. to form the reinforced gel.

EXAMPLE 2

Pluronic F-127 Gel in Water (20% w/w), Reinforced with Polyethylene Fibers 3 g of F-127 were dissolved in 12 g water at around 5° C. temperature, generating a 20% w/w solution. While at this temperature (below F-127's gelling temperature), 1 g of polyethylene fibers were added to the solution. The system was then heated at 37° C. to form the reinforced gel.

EXAMPLE 3

Pluronic F-127 Gel in Water (20% w/w), Reinforced with Kevlar Fibers 3 g of F-127 were dissolved in 12 g water at around 5° C. temperature, generating a 20% w/w solution. While at this temperature (below F-127's gelling temperature), 1 g of Kevlar 49 fibers were added to the solution. The system was then heated at 37° C. to form the reinforced gel.

EXAMPLE 4

Pluronic F-127 Gel in Water (20% w/w), Reinforced with Poly(L)lactic Acid (P(L)LA) Fibers 3 g of F-127 were dissolved in 12 g water at around 5° C. temperature, generating a 20% w/w solution. While at this temperature (below F-127's gelling temperature), 1 g of P(L)LA fibers were added to the solution. The system was then heated at 37° C. to form the reinforced gel.

EXAMPLE 5

Pluronic F-127 Gel in Water (20% w/w), Reinforced with Polyvinyl Alcohol Particles (300 γm)

3 g of F-127 were dissolved in 12 g water at around 5° C. temperature, generating a 20% w/w solution. While at this temperature (below F-127's gelling temperature), 1 g polyvinyl alcohol (PVA) particles, typically in the 300±100 micron size range, were added to the solution. The system was then heated at 37° C. to form the reinforced gel.

EXAMPLE 6

Pluronic F-127 Gel in Water (20% w/w), Reinforced with Poly(l)lactic Acid (P(L)LA) Particles (1-5 μm)

3 g of F-127 were dissolved in 12 g water at around 5° C. temperature, generating a 20% w/w solution. While at this temperature (below F-127's gelling temperature), 1 g poly(l) lactic acid particles (1-5 μm) were added to the solution. The system was then heated at 37° C. to form the reinforced gel.

EXAMPLE 7

Pluronic F-127 Gel in Water (20% w/w), Reinforced with Polypropylene Mesh 3 g of F-127 were dissolved in 12 g water at around 5° C. temperature, generating a 20% w/w solution. While at this temperature (below F-127's gelling temperature), 3 g of polypropylene mesh were added to the solution. The system was then heated at 37° C. to form the reinforced gel.

EXAMPLE 8

Pluronic F-127 Gel in Water (20% w/w), Reinforced with Carbon Fibers Unidirectional Fabric 3 g of F-127 were dissolved in 12 g water at around 5° C. temperature, generating a 20% w/w solution. While at this temperature (below F-127's gelling temperature), 2,4 g of carbon fibers unidirectional fabric were added to the solution. The system was then heated at 37° C. to form the reinforced gel.

EXAMPLE 9

Pluronic F-77 Gel in Water (20% w/w), Reinforced with Poly(l)lactic Acid Fibers 3 g of F-77 were dissolved in 12 g water at around 5° C. temperature, generating a 20% w/w solution. While at this temperature (below F-77's gelling temperature), 1 g of P(L)LA fibers were added to the solution. The system was then heated at 37° C. to form the reinforced gel.

EXAMPLE 10

Alternating Poly(ether-carbonate) [PEG6000-OCO-PPG3000]$_n$ Gel in Water (20% w/w), Reinforced with Poly(l)lactic Acid Fibers a) Synthesis of Alternating Poly(ether-carbonate) [PEG6000-OCO-PPG3000]$_n$ i) Synthesis of Triblock ClCO-PEG6000-COCl (PEG6000 Dichloroformate)

30.3 grams of dry PEG6000 (molecular weight 6,000) were dissolved in 50 ml dry chloroform in a 250 ml flask. 66 gram of a 3% w/w chloroformic solution of phosgene (100% molar excess to PEG) were added to the PEG and the mixture was allowed to react at 60° C. for 4 h, with magnetic stirring and a condenser in order to avoid solvent and phosgene evaporation. The reaction flask was connected to a NaOH trap (20% w/w solution in water/ethanol 1:1) in order to trap the phosgene that could be released during the reaction. Once the reaction was completed, the system was allowed to cool down to room temperature (RT) and the excess of phosgene was eliminated by vacuum. The FT-IR analysis showed the characteristic absorption band at 1777 $cm^{-1}$, belonging to the chloroformate group vibration.

ii) Synthesis of [-PEG6000-OCO-PEG3000-]$_n$ Polymer 15.15 grams of dry PPG3000 (molecular weight 3,000) were added to ClCO-PEG6000-COCl produced in i), at RT. The mixture was cooled to 5° C. in an ice bath and 6.3 grams pyridine dissolved in 20 ml chloroform, were added dropwise over a 15 min period. Then, the temperature was allowed to rise to RT and the reaction was continued for additional 45 minutes. After that, the temperature was risen to 35° C. and the reaction was continued for one additional hour. The polymer produced was separated from the reaction mixture by adding it to about 600 ml petroleum ether 40-60. The lower phase of the two-phase system produced was separated and dried at RT. Finally, the polymer was washed with portions of petroleum ether and dried, and a light yellow, brittle and water soluble powder was obtained. The material displayed a melting endotherm at 53.5° C. and the FT-IR analysis showed the characteristic carbonate group peak at 1746 cm-1. The molecular weight of the polymer produced was Mn 36,400 ($M_w/M_n$=1.28), as determined by GPC. The PEG/PPG block ratio in the final product was determined by $^1$H-NMR using a calibration curve obtained from different blends having various PEG6000/PPG3000 ratios and was 1.78.

b) Preparation of Alternating Poly(ether-carbonate) [PEG6000-OCO-PPG3000]$_n$ Gel in Water (20% w/w), Reinforced with Poly(l)lactic Acid Fibers 3 g of alternating polycarbonate [PEG6000-OCO-PPG3000]$_n$ were dissolved in 12 g water at around 5° C. temperature, generating a 20% w/w solution. While at this temperature (below the alternating polycarbonate's gelling temperature), 1 g poly(l)lactic acid fibers were added to the solution. The system was then heated at 37° C. to form the reinforced gel.

EXAMPLE 11

Alternating Poly(ether-carbonate) [PEG6000-OCO-PPG3000]$_n$ Gel in Water (20% w/w), Reinforced with Cellulose Particles (20 µm)

a) Synthesis of Alternating Poly(ether-carbonate) [PEG6000-OCO-PPG3000]$_n$

The synthesis of alternating poly(ether-carbonate) [PEG6000-OCO-PPG3000]$_n$ was performed as described in Example 10a.

b) Preparation of Alternating Poly(ether-carbonate) [PEG6000-OCO-PPG3000]$_n$ Gel in Water (20% w/w), Reinforced with Cellulose Particles (20 µm)

3 g of alternating poly(ether-carbonate) [PEG6000-OCO-PPG3000]$_n$ were dissolved in 12 g water at around 5° C. temperature, generating a 20% w/w solution. While at this temperature (below the alternating polycarbonate's gelling temperature), 1 g cellulose particles (20 □m) were added to the solution. The system was then heated at 37° C. to form the reinforced gel.

EXAMPLE 12

Alternating Poly(ether-carbonate) [PEG4000-OCO-PPG4000]$_n$ Gel in Water (20% w/w), Reinforced with Poly(l)lactic Acid (P(l)LA) Particles (1-5 µm)

a) Synthesis of Alternating Poly(ether-carbonate) [-PEG4000-OCO-PPG4000-]$_n$ i) Synthesis of Triblock CICO-PEG4000-COCI The procedure in Example 10 a)i) was substantially repeated, except that 20 grams (0.005 mol) PEG4000 (molecular weight 4,000) and 20 grams of a 7.7% w/w chloroformic solution of phosgene (100% molar excess to PEG), were used. The FT-IR analysis showed the characteristic absorption band at 1777 cm$^{-1}$, belonging to the chloroformate group vibration.

b) Synthesis of [-PEG4000-CO-PEG4000-]$_n$ Polymer

The procedure in Example 10 a)ii) was substantially repeated, except that 20 grams (0.005 mol) PEG4000 (molecular weight 4,000) and 7.9 grams pyridine, were used. A light yellow powder was obtained. The product showed a $T_g$ at −74° C. and $T_m$ at 50° C. and FT-IR analysis showed the characteristic peak at 1746 cm$^{-1}$. The polymer produced presented $M_n$ 25,500 ($M_w/M_n$=1.53). The PEG/PPG block ratio determined by $^1$H-NMR using a calibration curve obtained from different ratio PEG4000/PPG4000 blends and was 1.27.

b) Preparation of Alternating Poly(ether-carbonate) [PEG4000-OCO-PPG4000]$_n$ Gel in Water (20% w/w), Reinforced with Poly(l)lactic Acid Particles (1-5 µm)

3 g of alternating poly(ether-carbonate) were dissolved in 12 g water at around 5° C. temperature, generating a 20% w/w solution. While at this temperature (below the alternating polycarbonate's gelling temperature), 1 g poly(l)lactic acid particles (1-5 µm) were added to the solution. The system was then heated at 37° C. to form the reinforced gel.

EXAMPLE 13

Alternating Poly(ether-ester-carbonate) [(Caprolactone)$_4$-PEG6000-(Caprolactone)$_4$-OCO-PPG3000]$_n$ Gel in Water (20% w/w), Reinforced with Poly(l) lactic Acid (P(l)LA) Particles (1-5 µm)

a) Synthesis of (Caprolactone)$_4$-PEG6000-(Caprolactone)$_4$ Triblock 30.3 g of PEG6000 were dried at 120° C. under vacuum for 2 hours. Then, 10.1 g caprolactone and 0.05 g stannous 2-ethyl-hexanoate were added. The reaction mixture was heated at 145° C. for 2.5 hours in a dry nitrogen atmosphere. Finally, the reaction mixture was cooled to RT, dissolved in chloroform, precipitated in petroleum ether and dried at RT.

b) Synthesis of Alternating Poly(ether-ester-carbonate) [(Caprolactone)$_4$-PEG6000-(Caprolactone)$_4$-OCO-PPG3000]$_n$ a) Synthesis of CICO-(Caprolactone)$_4$-PEG6000-(Caprolactone)$_4$-COCI 40.1 grams of dry (Caprolactone)$_4$-PEG6000-(Caprolactone)$_4$ were dissolved in 50 ml dry chloroform in a 250 ml flask. 66 gram of a 3% w/w chloroformic solution of phosgene (100% molar excess to PEG) were added to the PEG and the mixture was allowed to react at 60° C. for 4 h, with magnetic stirring and a condenser in order to avoid solvent and phosgene evaporation. The reaction flask was connected to a NaOH trap (20% w/w solution in water/ethanol 1:1) in order to trap the phosgene that could be released during the reaction. Once the reaction was completed, the system was allowed to cool down to room temperature (RT) and the excess of phosgene was eliminated by vacuum. The FT-IR analysis showed the characteristic absorption band at 1777 cm$^{-1}$, belonging to the chloroformate gvibration.

ii) Synthesis of [(Caprolactone)$_4$-PEG6000-(Caprolactone)$_4$-OCO-PPG3000]$_n$ Polymer 15.2 grams of dry PPG3000 (molecular weight 3,000) were added to CICO-(Caprolactone)$_4$-PEG6000-(Caprolactone)$_4$-COCI produced in i), at RT. The mixture was cooled to 5° C. in an ice bath and 6.3 grams pyridine dissolved in 20 ml chloroform, were added dropwise over a 15 min period. Then, the temperature was allowed to rise to RT and the reaction was continued for additional 45 minutes. After that, the temperature was risen to 35° C. and the reaction was continued for one additional hour. The polymer produced was separated from the reaction mixture by adding it to about 600 ml petroleum ether 40-60. The lower phase of the two-phase system produced was separated and dried at RT. Finally, the polymer was washed with portions of petroleum ether and dried, and a light yellow, brittle and water soluble powder was obtained.

c) Preparation of Alternating Poly(ether-ester-carbonate) [(Caprolactone)$_4$-PEG6000-(Caprolactone)$_4$-OCO-PPG3000]$_n$ Gel in Water (20% w/w), Reinforced with Poly (l)lactic Acid Particles (1-5 µm)

3 g of alternating poly(ether-ester-carbonate) were dissolved in 12 g water at around 5° C. temperature, generating a 20% w/w solution. While at this temperature (below the alternating polycarbonate's gelling temperature), 1 g poly(l) lactic acid particles (1-5 µm) were added to the solution. The system was then heated at 37° C. to form the reinforced gel.

EXAMPLE 14

Preparation of Cross-linked Pluronic F-127 Dimethacrylate Gel in Water (20% w/w), Reinforced with Poly(l)lactic Acid Fibers a) Synthesis of Pluronic F-127 Dimethacrylate 40 g of F-127 were dried at 120° C. in vacuum for 2 hours. Then the polymer was dissolved in 75 ml dry chloroform and the solution was cooled to 0° C. in an ice bath and 2.63 g of triethylamine (TEA) were added. 2.65 g of recently distilled methacryloyl chloride were diluted in 20 ml chloroform and added dropwise for 2 hours into the cooled mixture under a dry nitrogen current. Finally, the reaction was allowed to proceed for 24 hours at RT. The crude product was dried under vacuum and was re-dissolved in hot toluene (100 ml). The hot mixture was filtered in order to eliminate the triethylammonium hydrochloride. The toluene solution was added to 400 ml of petroleum ether 60-80°. The white product was filtered and washed with several petroleum ether 40-60° portions and dried under vacuum at RT.

b) Cross-linking of F-127 Dimethacrylate in Water, Reinforced with Poly(l)lactic Acid Fibers 3 g of the polymer were dissolved in 12 g water at low temperature. 20 mg ammonium persulfate (APS) and 0.5 g poly(l)lactic acid fibers were added. The solution was cooled at 0° C. and dry nitrogen was bubbled, in order to eliminate the oxygen. Finally 0.5 N,N,N',N'-tetraethylethylene diamine (TEMED) were added and the mixture was incubated at 37° C. for 24 hours. The product was washed with water.

EXAMPLE 15

Preparation of Cross-linked Pluronic F-127 Dimethacrylate Gel in Water, Reinforced with Polyvinyl Alcohol Multi-methacrylate Particles (300 µm)

a) Synthesis of Polyvinyl Alcohol (PVA) Multi-methacrylate 5 g of PVA were suspended in 50 ml of dry chloroform, the suspension was cooled to 0° C. and 23.6 g triethylamine were added. 23.6 g of recently distilled methacryloyl chloride were diluted in 20 ml chloroform and added dropwise for 2 hours into the cooled mixture under a dry nitrogen current. Finally, the reaction was allowed to proceed for 24 hours at RT. The mixture was filtered and the white product was washed with chloroform portions and dried under vacuum.

b) Synthesis of Pluronic F-127 Dimethacrylate

The synthesis of Pluronic F-127 dimethacrylate was performed as described in Example 14 a).

c) Preparation of Cross-linked Pluronic F-127 Dimethacrylate in Water, Reinforced with Polyvinyl Alcohol Multi-methacrylate Particles (300 µm)

3 g of the Pluronic F-127 dimethacrylate were dissolved in 12 g water at at around 5° C. temperature. 20 mg ammonium persulfate (APS) and 0.5 g PVA-multimethacrylate particles were added. The solution was cooled at 0° C. and dry nitrogen was bubbled in order to eliminate the oxygen. Finally 0.5 N,N,N',N'-tetraethylethylene diamine (TEMED) were added and the mixture was incubated at 37° C. for 24 hours. The product was washed with water.

EXAMPLE 16

Pluronic F127 Matrix Reinforced with Polycaprolactone MW=530 (PCL530) Dimethacrylate Crosslinked Scaffold a) Synthesis of PCL530 Dimethacrylate 5 g of polycaprolactone diol MW=530 (PCL530) were dried at 120° C. in vacuum for 2 hours. Then the polymer was dissolved in 15 ml dry chloroform and the solution was cooled to 0° C. in an ice bath and 7.9 g of triethylamine (TEA) were added. 7.9 g of recently distilled methacryloyl chloride were diluted in 20 ml chloroform and added dropwise for 2 hours into the cooled mixture under a dry nitrogen current. Finally, the reaction was allowed to proceed for 24 hours at RT. The crude product was dried under vacuum and was re-dissolved in hot toluene (100 ml). The hot mixture was filtered in order to eliminate the triethylammonium hydrochloride. The toluene solution was added to 400 ml of petroleum ether 60-80°. The white product was filtered and washed with several petroleum ether 40-60° portions and dried under vacuum at RT.

a) Preparation of PCL530 di-IPTS Crosslinked Scaffold Within Pluronic F127 Matrix 0.8 g F127 were dissolved in 3.2 g PBS (pH=7.4, 0.1 M) at 4° C. 1 g PCL530 DMA were added and the mixture was homogeneized. 20 mg ammonium persulfate (APS). The solution was cooled at 0° C. and dry nitrogen was bubbled in order to eliminate the oxygen. Then 20 mg sodium metabisulfite were added and the mixture was incubated at 37° C.

EXAMPLE 17

Polycaprolactone-Polytetramethylene Glycol-Polycaprolactone (Terathane.$^{RTM}$ CL MW=2000, PTMG2000 CL) DMA Crosslinked Scaffold Within Pluronic F127 Matrix a) Synthesis of PTMG2000 CL DMA 20.2 g of PTMG2000 CL were dried at 120° C. in vacuum for 2 hours. Then the polymer was dissolved in 40 ml dry chloroform and the solution was cooled to 0° C. in an ice bath and 8.1 g of triethylamine (TEA) were added. 8.1 g of recently distilled methacryloyl chloride were diluted in 20 ml chloroform and added dropwise for 2 hours into the cooled mixture under a dry nitrogen current. Finally, the reaction was allowed to proceed for 24 hours at RT. The crude product was dried under vacuum and was re-dissolved in hot toluene (100 ml). The hot mixture was filtered in order to eliminate the triethylammonium hydrochloride. The toluene solution was added to 400 ml of petroleum ether 60-80°. The white product was filtered and washed with several petroleum ether 40-60° portions and dried under vacuum at RT.

b) Preparation of PTMG2000 CL DMA Crosslinked Scaffold Within Pluronic F127 Matrix 0.8 g F127 were dissolved in 3.2 g water at 4° C. Then, 1 g PTMG2000 CL DMA were added and the mixture was homogeneized. The solution was cooled at 0° C. and dry nitrogen was bubbled in order to eliminate the oxygen. Then 20 mg sodium metabisulfite were added and the mixture was incubated at 37° C.

EXAMPLE 18

Preparation of Cross-linked Pluronic F-77 Dimethacrylate in Water, Reinforced with Glass Multi-methacrylate Fibers (Using TEMED as Activator)

a) Synthesis of Glass Fibers Multi-methacrylate 5,5 g of glass fibers were suspended in 50 ml of dry chloroform, the suspension was cooled to 0° C. and 23.6 g triethylamine were added. 23.6 g of recently distilled methacryloyl chloride were diluted in 20 ml chloroform and added dropwise for 2 hours into the cooled mixture under a dry nitrogen current. Finally, the reaction was allowed to proceed for 24 hours at RT.

The mixture was filtered and the fibers were washed with chloroform portions and dried under vacuum.

b) Synthesis of F-77 Dimethacrylate 40 g of F-77 were dried at 120° C. in vacuum for 2 hours. Then the polymer was dissolved in 50 ml dry chloroform and the solution was cooled to 0° C. in an ice bath and 4.9 g of triethylamine (TEA) were added. 4.9 g of recently distilled methacryloyl chloride were diluted in 20 ml chloroform and added dropwise for 2 hours into the cooled mixture unda dry nitrogen current. Finally, the reaction was allowed to proceed for 24 hours at RT. The crude product was dried under vacuum and was re-dissolved in hot toluene (100 ml). The hot mixture was filtered in order to eliminate the triethylammonium chloride. The toluene solution was added to 400 ml of petroleum ether 60-80°. The white product was filtered and washed with several petroleum ether 40-60° portions and dried in vacuum at RT.

c) Preparation of Cross-linked Pluronic F-77 Dimethacrylate in Water, Reinforced with Glass Multi-methacrylate Fibers (Using TEMED as Activator)

3 g of F-77 dimethacrylate were dissolved in 12 g water at 5° C. low temperature. 20 mg ammonium persulfate (APS) and 0.6 g glass multi-methacrylate fibers were added. Dry nitrogen was bubbled in order to eliminate the oxygen. Then 0.5 g TEMED were added and the mixture was incubated at 37° C. The cross-linked system was washed with water.

EXAMPLE 19

Preparation of Cross-linked Pluronic F-77 in Water, Reinforced with Polyvinylalcohol Multi-methacrylate Particles (300 μm) (Using Sodium Metabisulfite (SBS) as Activator)

a) Synthesis of Polyvinylalcohol (PVA) Multimethacrylate

The synthesis of polyvinylalcohol (PVA) multimethacrylate was carried out as described in Example 14 a).

b) Synthesis of F-77 Dimethacrylate

The synthesis of F-77 dimethacrylate was carried out as described in Example 15 a).

c) Preparation of Cross-linked Pluronic F-77 Dimethacrylate in Water, Reinforced with PVA Multi-methacrylate Particles (300 μm) (Using Sodium Metabisulfite (SBS) as Activator)

3 g of F-77 dimethacrylate were dissolved in 12 ml of water. 20 mg ammonium persulfate (APS) and 0.5 g PVA-multimethacrylate particles were added. Dry nitrogen was bubbled in order to eliminate the oxygen. Then 20 mg sodium metabisulfite were added and the mixture was incubated at 37° C. The cross-linked system was washed with water.

EXAMPLE 20

Preparation of Cross-linked Pluronic F-77 in Water, Reinforced with Glass Multi-methacrylate Fibers (Using Vitamin C and Iron(II) Sulfate as Activator)

a) Synthesis of Glass Multi-methacrylate Fibers

The synthesis of glass multi-methacrylate fibers was described in Example 15a).

b) Synthesis of F-77 Dimethacrylate

The synthesis of F-77 dimethacrylate was carried out as described in Example 15 b).

c) Preparation of Cross-linked Pluronic F-77 Dimethacrylate in Water, Reinforced with Glass Multi-methacrylate Fibers (Using Vitamin C and Iron(II) Sulfate as Activator)

3 g of F-77 dimethacrylate were dissolved in 12 ml of water. 20 mg ammonium persulfate (APS) and 0.5 g glass multi-methacrylate fibers were added. Dry nitrogen was bubbled in order to eliminate the oxygen. Then 5 mg Vitamin C and 5 mg iron(II) sulfate heptahydrate were added and the mixture was incubated at 37° C. The cross-linked system was washed with water.

EXAMPLE 21

Preparation of Cross-linked Pluronic L-44 in Water, Reinforced with Glass Multi-methacrylate Fibers (Using Vitamin C and Iron(II) Sulfate as Activator)

a) Synthesis of Glass Multi-methacrylate Fibers

The synthesis of glass multi-methacrylate fibers was carried out as described in Example 15 a).

b) Synthesis of Pluronic L-44 Dimethacrylate 41.4 g of L-44 were dried at 120° C. in vacuum for 2 hours. Then the polymer was dissolved in 50 ml dry chloroform and the solution was cooled to 0° C. in an ice bath and 8.3 g of triethylamine (TEA) were added. 8.3 g of recently distilled methacryloyl chloride were diluted in 20 ml chloroform and added dropwise for 2 hours into the cooled mixture under a dry nitrogen current. Finally, the reaction was allowed to proceed for 24 hours at RT.

The crude product was dried under vacuum and was re-dissolved in hot toluene (100 ml). The hot mixture was filtered in order to eliminate the triethylammonium chloride. The toluene solution was added to 400 ml of petroleum ether 60-80°. The lower liquid product was separated by decantation, washed with several petroleum ether 40-60° portions and dried under vacuum at RT.

c) Preparation of Cross-linked Pluronic L-44 Dimethacrylate in Water, Reinforced with Glass Multi-methacrylate Fibers (Using Vitamin C and Iron(II) Sulfate as Activator)

3 g of L-44 dimethacrylate were dissolved in 12 ml of water. 20 mg ammonium persulfate (APS) and 0.5 g glass multi-methacrylate fibers were added. Dry nitrogen was bubbled in order to eliminate the oxygen. Then 5 mg Vitamin C and 5 mg iron(II) sulfate heptahydrate were added and the mixture was incubated at 37° C. The cross-linked system was washed with water.

EXAMPLE 22

Preparation of Cross-linked Pluronic F-38 in Water, Reinforced with Polyvinyl Alcohol Multi-methacrylate Particles (300 µm) (Using Vitamin C and Iron(II) Sulfate as Activator)

c) Synthesis of Polyvinylalcohol (PVA) Multi-methacrylate Particles

The synthesis of polyvinylalcohol (PVA) multi-methacrylate was carried out as described in Example 14 a).

b) Synthesis of Pluronic F-38 Dimethacrylate 60 g of F-38 were dried at 120° C. in vacuum for 2 hours. Then the polymer was diluted in 75 ml dry chloroform and the solution was cooled to 0° C. in an ice bath and 10.8 g of triethylamine (TEA) were added. 10.8 g of recently distilled methacryloyl chloride were diluted in 20 ml chloroform and added dropwise for 2 hours into the cooled mixture under a dry nitrogen current. Finally, the reaction was allowed to proceed for 24 hours at RT.

The crude product was dried by vacuum and was re-dissolved in hot toluene (100 ml). The hot mixture was filtered in order to eliminate the triethylammonium chloride. The toluene solution was added to 400 ml of petroleum ether 60-80°. The white product was filtered and washed with several petroleum ether 40-60° portions and dried in vacuum at RT.

c) Preparation of Cross-linked Pluronic F-38 Dimethacrylate in Water, Reinforced with PVA Multi-methacrylate Particles (Using Vitamin C and Iron(II) Sulfate as Activator)

3 g of F-38 dimethacrylate were dissolved in 12 ml of water. 20 mg ammonium persulfate (APS) and 0.5 g PVA multi-methacrylate particles were added. Dry nitrogen was bubbled in order to eliminate the oxygen. Then 5 mg Vitamin C and 5 mg iron(II) sulfate heptahydrate were added and the mixture was incubated at 37° C. The cross-linked system was washed with water.

EXAMPLE 23

Preparation of Cross-linked Alternating Poly(ether-carbonate) [PEG6000-OCO-PPG3000]$_n$ in Water, Reinforced with Glass Multi-methacrylate Fibers (Using Vitamin C and Iron(II) Sulfate as Activator)

d) Synthesis of Glass Multi-methacrylate Fibers

The synthesis of glass multi-methacrylate fibers was carried out as described in Example 15 a).

b) Synthesis of Alternating Poly(ether-carbonate) [PEG6000-OCO-PPG3000]$_n$

The synthesis of alternating poly(ether-carbonate) [PEG6000-OCO-PPG3000]$_n$ was carried out as described in Example 10 a).

c) Synthesis of Alternating Poly(ether-carbonate) [PEG6000-OCO-PPG3000]$_n$ Dimethacrylate 14 g of alternating poly(ether-carbonate) [PEG6000-OCO-PPG3000]$_n$ were dissolved in 50 ml dry chloroform, the solution was cooled to 0° C. in an ice bath and 1.4 g of triethylamine (TEA) were added. 1.4 g of recently distilled methacryloyl chloride were diluted in 20 ml chloroform and added dropwise for 2 hours into the cooled mixture under a dry nitrogen current. Finally, the reaction was allowed to proceed for 24 hours at RT.

The crude product was dried under vacuum and was re-dissolved in hot toluene (100 ml). The hot mixture was filtered in order to eliminate the triethylammonium chloride. The toluene solution was added to 400 ml of petroleum ether 60-80°. The light yellow product was filtered and washed with several petroleum ether 40-60° portions and dried in vacuum at RT.

d) Preparation of Cross-linked Alternating Poly(ether-carbonate) [PEG6000-OCO-PPG3000]$_n$ Dimethacrylate in Water, Reinforced with Glass Multi-methacrylate Fibers (Using Vitamin C and Iron(II) Sulfate as Activator)

3 g of alternating poly(ether-carbonate) [PEG6000-OCO-PPG3000]$_n$ dimethacrylate were dissolved in 12 ml water. 20 mg ammonium persulfate (APS) and 0.5 g glass multi-methacrylate fibers were added. Dry nitrogen was bubbled in order to eliminate the oxygen. The 5 mg Vitamin C and 5 mg iron(II) sulfate heptahydrate were added and the mixture was incubated at 37° C. The cross-linked system was washed with water.

EXAMPLE 24

Preparation of Poly(ether-carbonate) [PEG6000-OCO-PPG3000]$_n$ Dimethacrylate/Pluronic F-38 Dimethacrylate Cross-linked System Reinforced with Glass Multi-methacrylate Fibers (Using Vitamin C and Iron(II) Sulfate as Activator)

The synthesis of glass multi-methacrylate fibers was carried out as described in Example 15 a). The synthesis of F-38 dimethacrylate and the polycarbonate [PEG6000-OCO-PPG3000]$_n$ dimethacrylate described in Examples 19a and 20c, respectively.

1.2 g of alternating poly(ether-carbonate) [PEG6000-OCO-PPG3000]$_n$ dimethacrylate and 1.8 g of F-38 dimethacrylate were dissolved in 12 ml water. 20 mg ammonium persulfate (APS) and 0.5 g glass multi-methacrylate fibers were added. Then 5 mg Vitamin C and 5 mg iron(II) sulfate were added and the mixture was incubated at 37° C. Dry nitrogen was bubbled in order to eliminate the oxygen. The cross-linked system was washed with water.

EXAMPLE 25

Preparation of Cross-linked Degradable Pluronic (Lactoyl)$_4$-F-38-(Lactoyl)$_4$ in Water, Reinforced with PVA Multi-methacrylate Particles (300 µm) (Using Vitamin C and Iron(II) Sulfate as Activator)

a) Synthesis of Polyvinylalcohol (PVA) Multimethacrylate Particles

The synthesis of polyvinyl alcohol (PVA) multimethacrylate was carried out as described in Example 14 a).

b) Synthesis of Pluronic (Lactoyl)$_4$-F-38-(Lactoyl)$_4$ 40 g of F-38 were dried at 120° C. in vacuum for 2 hours. Then, 5.3 g L-lactide and 0.1 g stannous 2-ethyl-hexanoate were added. The reaction mixture was heated at 145° C. for 2.5 hours in a dry nitrogen atmosphere. Finally, the reaction mixture was cooled to RT.

c) Synthesis of Pluronic (Lactoyl)$_4$-F-38-(Lactoyl)$_4$ Dimethacrylate 45.3 g of (Lactoyl)$_4$-F-38-(Lactoyl)$_4$ were dissolved in 50 ml chloroform, the solution was cooled to 0° C. in an ice bath and 7.2 g of triethylamine (TEA) were added. 7.2 g of recently distilled methacryloyl chloride were dissolved in 20 ml chloroform and added dropwise for 2 hours into the cooled mixture under a dry nitrogen current. Finally, the reaction was allowed to proceed for 24 hours at RT.

The crude product was dried under vacuum and was re-dissolved in hot toluene (100 ml). The hot mixture was filtered in order to eliminate the triethylammonium chloride. The toluene solution was added to 400 ml of petroleum ether 60-80°. The white product was filtered and washed with several petroleum ether 40-60° portions and dried in vacuum at RT.

d) Preparation of Cross-linked Degradable Pluronic (Lactoyl)$_4$-F-38-(Lactoyl)$_4$ in Water, Reinforced with PVA Multimethacrylate Particles (Using Vitamin C and Iron(II) Sulfate as Activator)

3 g of (Lactoyl)$_4$-F-38-(Lactoyl)$_4$ dimethacrylate were dissolved in 12 ml of water. 20 mg ammonium persulfate (APS) and 0.5 g PVA-multimethacrylate particles were added. Dry nitrogen was bubbled in order to eliminate the oxygen. Then 5 mg Vitamin C and 5 mg iron(II) sulfate heptahydrate were added and the mixture was incubated at 37° C. The cross-linked system was washed with water.

EXAMPLE 26

Preparation of Cross-linked Degradable Pluronic (Lactoyl)$_4$-F-77-(Lactoyl)$_4$ in Water, Reinforced with Glass Multi-methacrylate Fibers (Using Vitamin C and Iron(II) Sulfate as Activator)

a) Synthesis of Glass Multi-methacrylate Fibers

The synthesis of glass multi-methacrylate fibers was carried out as described in Example 15 a).

b) Synthesis of Pluronic (Lactoyl)$_4$-F-77-(Lactoyl)$_4$ 40 g of F-77 were dried at 120° C. in vacuum for 2 hours. Then 3.8 g L-lactide and 0.1 g stannous 2-ethyl-hexanoate were added. The reaction mixture was heated at 145° C. for 2.5 hours in a dry nitrogen atmosphere. Finally the reaction mixture was cooled to RT.

c) Synthesis of Pluronic (Lactoyl)$_4$-F-77-(Lactoyl)$_4$ Dimethacrylate 43.8 g of (Lactoyl)$_4$-F-77-(Lactoyl)$_4$ were dissolved in 50 ml chloroform, the solution was cooled to 0° C. in an ice bath and 4.9 g of triethylamine (TEA) were added. 4.9 g of recently distilled methacryloyl chloride were dissolved in 20 ml chloroform and added dropwise for 2 hours into the cooled mixture under a dry nitrogen current. Finally, the reaction was allowed to proceed for 24 hours at RT.

The crude product was dried by vacuum and was re-dissolved in hot toluene (100 ml). The hot mixture was filtered in order to eliminate the triethylammonium chloride. The toluene solution was added to 400 ml of petroleum ether 60-80°. The white product was filtered and washed with several petroleum ether 40-60° portions and dried in vacuum at RT.

d) Preparation of Cross-linked Degradable Pluronic (Lactoyl)$_4$-F-77-(Lactoyl)$_4$ in Water, Reinforced with Glass Multi-methacrylate Fibers (Using Vitamin C and Iron(II) Sulfate as Activator)

3 g of (Lactoyl)$_4$-F-77-(Lactoyl)$_4$ dimethacrylate were dissolved in 12 ml of water. 20 mg ammonium persulfate (APS) and 0.5 g glass multi-methacrylate fibers were added. Dry nitrogen was bubbled in order to eliminate the oxygen. Then 5 mg Vitamin C and 5 mg iron(II) sulfate heptahydrate were added and the mixture was incubated at 37° C. The cross-linked system was washed with water.

EXAMPLE 27

Preparation of Cross-linked Degradable Pluronic (Lactoyl)$_4$-F-127-(Lactoyl)$_4$ in Water, Reinforced Cellulose Multi-methacrylate Particles (20 μm) (Using Vitamin C and Iron(II) Sulfate as Activator)

a) Synthesis of Cellulose Multi-methacrylate Particles 15 g of cellulose (20 μm) were suspended in 50 ml of dry chloroform, the suspension was cooled to 0° C. and 64.2 g triethylamine were added. Then 64.2 g of recently distilled methacryloyl chloride were diluted in 30 ml chloroform and added dropwise for 2 hours into the cooled mixture under a dry nitrogen current. Finally, the reaction was allowed to proceed for 24 hours at RT. The fine white precipitate was filtered, washed several times with chloroform and dried at RT.

b) Synthesis of Pluronic (Lactoyl)$_4$-F-127-(Lactoyl)$_4$ 40 g of F-127 were dried at 120° C. in vacuum for 2 hours. Then 2.0 g L-lactide and 0.05 g stannous 2-ethyl-hexanoate were added. The reaction mixture was heated at 145° C. for 2.5 hours in a dry nitrogen atmosphere. Finally the reaction mixture was cooled to RT.

c) Synthesis of Pluronic (Lactoyl)$_4$-F-127-(Lactoyl)$_4$ Dimethacrylate 42.0 g of (Lactoyl)$_4$-F-127-(Lactoyl)$_4$ were dissolved in 50 ml chloroform, the solution was cooled to 0° C. in an ice bath and 4.9 g of triethylamine (TEA) were added. 4.9 g of recently distilled methacryloyl chloride were dissolved in 20 ml chloroform and added dropwise for 2 hours into the cooled mixture under a dry nitrogen current. Finally, the reaction was allowed to proceed for 24 hours at RT.

The crude product was dried by vacuum and was re-dissolved in hot toluene (100 ml). The hot mixture was filtered in order to eliminate the triethylammonium chloride. The toluene solution was added to 400 ml of petroleum ether 60-80°. The white product was filtered and washed with several petroleum ether 40-60° portions and dried in vacuum at RT.

d) Preparation of Cross-linked Degradable Pluronic (Lactoyl)$_4$-F-127-(Lactoyl)$_4$ in Water, Reinforced with Cellulose Multi-methacrylate Particles (Using Vitamin C and Iron(II) Sulfate as Activator)

3 g of (Lactoyl)$_4$-F-127-(Lactoyl)$_4$ dimethacrylate were dissolved in 12 ml of water. 20 mg ammonium persulfate (APS) and 0.5 g of cellulose multi-methacrylate_were added. Dry nitrogen was bubbled in order to eliminate the oxygen. Then 5 mg Vitamin C and 5 mg iron(II) sulfate heptahydrate were added and the mixture was incubated at 37° C. The cross-linked system was washed with water.

e) Hydrolysis Test Cross-linked Degradable Pluronic (Lactoyl)$_4$-F-127-(Lactoyl), Reinforced with Cellulose Multi-methacrylate Particles in Water The hydrolysis test was performed as follows: the cross-linked gel was stored at 37° C. for several months. The linkage of the ester bonds between the F-127 molecule and the cross-linked methacrylate group generated newly a RTG system.

EXAMPLE 28

Preparation of Cross-linked Pluronic F-38 in Water, Reinforced with Cellulose Multi-methacrylate Particles (20 μm) (Using Vitamin C and Iron(II) Sulfate as Activator)

a) Synthesis of Cellulose Multi-methacrylate Particles

The synthesis of cellulose multi-methacrylate was carried out as described in Example 25 a).

b) Synthesis of Pluronic F-38 Dimethacrylate

The synthesis of Pluronic F-38 dimethacrylate was carried out as described in Example 20b).

c) Preparation of Cross-linked Degradable Pluronic F-38 in Water, Reinforced with Cellulose Multi-methacrylate Particles (20 µm) (Using Vitamin C and Iron(II) Sulfate as Activator)

3 g of F-38 dimethacrylate were dissolved in 12 ml of water. 20 mg ammonium persulfate (APS) and 0.5 g PVA-multimethacrylate particles were added. Dry nitrogen was bubbled in order to eliminate the oxygen. Then 5 mg Vitamin C and 5 mg iron(II) sulfate heptahydrate were added and the mixture was incubated at 37° C. The cross-linked system was washed with water.

EXAMPLE 29

Preparation of Cross-linked Alternating Poly(ether-ester-carbonate) [(Caprolactone)$_4$-PEG6000-(Caprolactone)$_4$-OCO-PPG3000]$_n$ in Water, Reinforced with Cellulose Multi-methacrylate Particles (20 µm) (Using Vitamin C and Iron(II) Sulfate as Activator)

a) Synthesis of Cellulose Multi-methacrylate Particles

The synthesis of cellulose multi-methacrylate particles was carried out as described in Example 25 a).

b) Synthesis of Alternating Poly(ether-ester-carbonate) [(Caprolactone)$_4$-PEG6000-(Caprolactone)$_4$-OCO-PPG3000]$_n$ The synthesis of alternating poly(ether-ester-carbonate) [(Caprolactone)$_4$-PEG6000-(Caprolactone)$_4$-OCO-PPG3000]$_n$ was carried out as described in Example 13b).

c) Synthesis of Alternating Poly(ether-ester-carbonate) [(Caprolactone)$_4$-PEG6000-(Caprolactone)$_4$-OCO-PPG3000]$_n$ Dimethacrylate 15.4 g of alternating poly(ether-ester-carbonate) [(Caprolactone)$_4$-PEG6000-(Caprolactone)$_4$-OCO-PPG3000]$_n$ were dissolved in 50 ml dry chloroform, the solution was cooled to 0° C. in an ice bath and 1.4 g of triethylamine (TEA) were added. 1.4 g of recently distilled methacryloyl chloride were diluted in 20 ml chloroform and added dropwise for 2 hours into the cooled mixture under a dry nitrogen current. Finally, the reaction was allowed to proceed for 24 hours at RT.

The crude product was dried under vacuum and was re-dissolved in hot toluene (100 ml). The hot mixture was filtered in order to eliminate the triethylammonium chloride. The toluene solution was added to 400 ml of petroleum ether 60-80°. The light yellow product was filtered and washed with several petroleum ether 40-60° portions and dried in vacuum at RT.

d) Preparation of Cross-linked Alternating Poly(ether-ester-carbonate) [(Caprolactone)$_4$-PEG6000-(Caprolactone)$_4$-OCO-PPG3000]$_n$ Dimethacrylate in Water, Reinforced with Cellulose Multi-methacrylate Particles (20 µm) (Using Vitamin C and Iron(II) Sulfate as Activator)

3 g of alternating poly(ether-carbonate) [PEG6000-OCO-PPG3000]$_n$ dimethacrylate were dissolved in 12 ml water. 20 mg ammonium persulfate (APS) and 0.5 g cellulose multi-methacrylate particles (20 µm) were added. Dry nitrogen was bubbled in order to eliminate the oxygen. Then 5 mg Vitamin C and 5 mg iron(II) sulfate heptahydrate were added and the mixture was incubated at 37° C. The cross-linked system was washed with water.

e) Hydrolysis Test of Cross-linked Alternating Poly(ether-ester-carbonate) [(Caprolactone)$_4$-PEG6000-(Caprolactone)$_4$-OCO-PPG3000]$_n$ Dimethacrylate in Water, Reinforced with Cellulose Multi-methacrylate Particles (20 µm).

The hydrolysis test was performed as follows: the cross-linked gel was stored at 37° C. for several months. The linkage of the ester bonds between the [(Caprolactone)$_4$-PEG6000-(Caprolactone)$_4$-OCO-PPG3000]$_n$ molecule and the cross-linked methacrylate group and the caprolactone blocks resulted in the total degradation of the system with the total loss of the Theological properties.

EXAMPLE 30

Preparation of Cross-linked Degradable Pluronic F-38 in Water, Reinforced with a Knitted PET Fabric (Diameter 10 mm, Length 20 mm) (Using Vitamin C and Iron(II) Sulfate as Activator)

a) Synthesis of Pluronic F-38 Dimethacrylate

The synthesis of Pluronic F-38 dimethacrylate was carried out as described in Example 20b).

b) Preparation of Cross-linked Degradable Pluronic F-38 in Water, Reinforced with a Knitted PET Fabric (Diameter 10 mm, Length 20 mm) (Using Vitamin C and Iron(II) Sulfate as Activator)

3 g of Pluronic F-38 dimethacrylate were dissolved in 12 ml water. 20 mg ammonium persulfate (APS) were added to the solution and a knitted PET fabric (diameter 10 mm, length 20 mm) was introduced perpendicularly in the container. Dry nitrogen was bubbled in order to eliminate the oxygen. Then, 5 mg Vitamin C and 5 mg iron(II) sulfate heptahydrate were added and the mixture was incubated at 37° C. The cross-linked system was washed with water.

EXAMPLE 31

Preparation of Cross-linked Pluronic F-38 in Water, Reinforced with Oriented Polyethylene Fibers (Using Vitamin C and Iron(II) Sulfate as Activator)

a) Synthesis of Pluronic F-38 Dimethacrylate

The synthesis of Pluronic F-38 dimethacrylate was carried out as described in Example 20b).

b) Preparation of Cross-linked Pluronic F-38 in Water, Reinforced with Oriented Polyethylene Fibers (Using Vitamin C and Iron(II) Sulfate as Activator)

0.1 g of polyethylene fibers were placed at the center of a 3 ml cylindrical glass mold, generating an oriented, central fiber reinforcing phase.

0.40 g of Pluronic F-38 dimethacrylate were dissolved in 2.4 g water in order to achieve a 20% solution. 20 mg ammonium persulfate (APS) were added to the solution and the mixture was introduced into the mold. Then, 5 mg Vitamin C and 5 mg iron(II) sulfate heptahydrate were added and the mixture was incubated at 37° C. The reinforced cross-linked system was washed with water.

EXAMPLE 32

Preparation of Cross-linked Pluronic F-127 Dimethacrylate Gel in Water (15% w/w), Reinforced with poly(l)lactic Acid Fibers a) Synthesis of Pluronic F-127 Dimethacrylate The synthesis of Pluronic F-127 dimethacrylate was performed as described in Example 14 a).

b) Cross-linking of F-127 Dimethacrylate in Water (15% w/w), Reinforced with Poly(l)lactic Acid Fibers 2.3 g of the polymer were dissolved in 12.8 g water at low temperature. 20 mg ammonium persulfate (APS) and 0.5 g poly(l)lactic acid fibers were added. The solution was cooled at 0° C. and dry nitrogen was bubbled, in order to eliminate the oxygen. Finally 0.5 N,N,N',N'-tetraethylethylene diamine (TEMED) were added and the mixture was incubated at 37° C. for 24 hours. The product was washed with water.

EXAMPLE 33

Preparation of Cross-linked Pluronic F-127 Dimethacrylate Gel in Water (30% w/w), Reinforced with poly(l)lactic Acid Fibers a) Synthesis of Pluronic F-127 Dimethacrylate The synthesis of Pluronic F-127 dimethacrylate was performed as described in Example 14 a).

b) Cross-linking of F-127 Dimethacrylate in Water (30% w/w), Reinforced with Poly(l)lactic Acid Fibers 4.5 g of the F-127 dimethacrylate were dissolved in 10.5 g water at low temperature. 20 mg ammonium persulfate (APS) and 0.5 g poly(l)lactic acid fibers were added. The solution was cooled at 0° C. and dry nitrogen was bubbled, in order to eliminate the oxygen. Finally 0.5 N,N,N',N'-tetraethylethylene diamine (TEMED) were added and the mixture was incubated at 37° C. for 24 hours. The product was washed with water.

EXAMPLE 34

Water Up-take of the Cross-linked Reinforced Polymers

Polymer A: Cross-linked Pluronic F-77, 20% without reinforcement (this polymer was used as the control).

Polymer B: Cross-linked Pluronic F-77, 20% reinforced with PVA particles (300 γm).

Polymer C: Cross-linked Pluronic F-77, 20% reinforced with PVA multimethacrylate particles (300 γm).

The table presents the water up-take process (in % w/w) at 37° C.

| Time    | Polymer A | Polymer B | Polymer C |
|---------|-----------|-----------|-----------|
| 5 min.  | 47        | 38        | 35        |
| 15 min. | 76        | 60        | 55        |
| 30 min. | 102       | 76        | 68        |
| 1 h.    | 152       | 106       | 93        |
| 3 h.    | 275       | 189       | 166       |
| 6 h.    | 388       | 251       | 219       |
| 19 h.   | 536       | 315       | 287       |
| 25 h.   | 544       | 318       | 295       |
| 43 h.   | 569       | 328       | 315       |
| 118 h.  | 584       | 331       | 320       |

EXAMPLE 35

Compression Test of Different Cross-linked Reinforced Pluronic F-38

The test was carried Out as described by Gregson et al. (Carbohydrate Polymers 38:255 1999) and is illustrated schematically in FIG. 1.

Where,

R, radius of container: 30 mm.

L, sample thickness: 10 mm.

r, radius of the probe: 12 mm.

δ, depth of penetration: 0.3 mm.

F, applied force: measured variable from curve slope in N/mm.

Sample 1: Cross-linked Pluronic F-38 20% (1 $g_{polymer}$/5 $g_{total}$) without any reinforcement (this sample was used as the control).

Sample 2: Cross-linked Pluronic F-38 20% (1 $g_{polymer}$/5 $g_{total}$) reinforced with 0.13 g PVA particles.

Sample 3: Cross-linked Pluronic F-38 20% (1 $g_{polymer}$/5 $g_{total}$) reinforced with 0.50 g PVA particles.

Sample 4: Cross-linked Pluronic F-38 20% (1 $g_{polymer}$/5 $g_{total}$) reinforced with 0.75 g PVA particles.

Sample 5: Cross-linked Pluronic F-38 20% (1 $g_{polymer}$/5 $g_{total}$) with 0.13 g cellulose (20 mm) multi-methacrylate reinforcement.

Sample 6: Cross-linked Pluronic F-38 20% (1 $g_{polymer}$/5 $g_{total}$) reinforced with 0.13 g glass fibers.

| Sample | Slope [N/mm] |
|--------|--------------|
| 1      | 11.8         |
| 2      | 15.5         |
| 3      | 17.5         |
| 4      | 19.4         |
| 5      | 15.5         |
| 6      | 20.9         |

EXAMPLE 26

Compression Test of Different Cross-linked Reinforced Pluronic F-77

Sample 1: Cross-linked Pluronic F-77 20% (1 $g_{polymer}$/5 $g_{total}$) without any reinforcement (this sample was used as the control).

Sample 2: Cross-linked Pluronic F-77 20% (1 $g_{polymer}$/5 $g_{total}$) reinforced with 0.13 g PVA particles.

Sample 3: Cross-linked Pluronic F-77 20% (1 $g_{polymer}$/5 $g_{total}$) reinforced with 0.13 g PLA particles (1-5 γm).

| Sample | Slope [N/mm] |
|--------|--------------|
| 1      | 5.1          |
| 2      | 8.1          |
| 3      | 6.0          |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A polymeric system, comprising:
   a polymeric component capable of undergoing a transition that results in a sharp increase in viscosity in response to a triggering effect of a temperature increase from a lower temperature to a temperature of about 37° C. and wherein said polymeric component is a block copolymer comprising polyethylene oxide (PEO) and polypropylene oxide (PPO) selected from the group consisting of a diblock, a triblock, and a segmented block copolymer comprising polyethylene oxide (PEG) and polypropylene oxide (PPO) chains connected via chain extenders;
   a solid, non-ceramic reinforcing component which reinforces the polymeric component and wherein said reinforcing component is a macro, micro or nano-sized polymer material comprising methacrylic polymers or polyesters; and
   a water-based solvent; wherein the viscosity of said polymeric component increases by at least about two times upon exposure of said polymeric system to said temperature increase.

2. The polymeric system of claim 1, wherein said polymeric component is biodegradable.

3. The polymeric system of claim 1, wherein said polymeric component is crosslinkable in situ by effecting changes in heat, ionic strength, and pH and wherein cross-linking bonding is selected from the group consisting of covalent, secondary and ionic bonding.

4. The polymeric system of claim 3, wherein said cross-linking bonding is temporary so that said polymeric component is able to essentially revert in situ, to a non-crosslinked state.

5. The polymeric system of claim 1, wherein said reinforcing component is polymeric.

6. The responsive polymeric system of claim 1, wherein said responsive polymeric component contains a molecule/s, to be delivered into the body.

7. The responsive polymeric system of claim 1, wherein said responsive polymeric component contains living cells selected from a group consisting of endothelial cells, hepatocytes, astrocytes, myocytes, osteoblasts, chondrocytes, epithelial cells, smooth muscles cells and/or combinations thereof.

8. The polymeric system of claim 1, wherein said polymeric component serves as a matrix for the release of molecules and for cell differentiation, proliferation and growth.

9. The polymeric system of claim 1, wherein said reinforcing component is biodegradable.

10. The responsive polymeric system of claim 1, wherein said solid reinforcing component is selected from a group consisting of a polyoxyalkylene polymer, a block copolymer comprising polyethylene oxide (PEO) and polypropylene oxide (PPO) selected from a group consisting of a diblock, a triblock or a multiblock, a segmented block copolymer comprising polyethylene oxide (PEO) and polypropylene oxide (PPO) chains, wherein said PEO and PPO chains are connected via a chain extender, a poly(alkyl-co-oxyalkylene) copolymer having the formula R—$(OCH_2CH)_n$—OH, where R is an hydrophobic group, a poly(N-alkyl substituted acrylamide), cellulose and cellulose derivatives and combinations thereof.

11. The responsive polymeric system of claim 1, wherein said solid reinforcing component is generated in situ.

12. The responsive polymeric system of claim 11, wherein said solid reinforcing component is introduced into the body as a non-viscous telechelic monomer, oligomer or polymer and becomes a solid at a predetermined body site.

13. The responsive polymeric system of claim 11, wherein said solid reinforcing component is introduced into the body as a telechelic water soluble monomer, oligomer or polymer, wherein said telechelic water soluble monomer, oligomer or polymer is deployed as a water solution and becomes a solid at a predetermined body site.

14. The responsive polymeric system of claim 1, wherein said solid reinforcing component is introduced as a water soluble monomer, oligomer or polymer such as poly(ethylene glycol) chains or any water soluble PEO-containing copolymer such PEO-PPO-PEO, PPO-PEO-PPO, PTMO-PEO-PTMO, PLA-PEO-PLA, PEO-PLA-PEO, PCL-PEO-PCL, PEO-PCL-PEO or any other telechelic water soluble oligomers or polymers containing segments such as vinyl alcohol, acrylic acid, methacrylic acid, acrylamide, N-vinyl pyrrolidone, oligo or polysaccharides, amino acids, oligopeptides, peptides or proteins, comprising double bond reactive groups such as acrylates or methacrylates or any other group able to react in a predetermined body site, and said water soluble molecule is reacted in situ to generate the solid reinforcement.

15. The polymeric system of claim 1, wherein at least one said polymeric component is cross-linked using techniques and equipment normally used or especially modified in minimally invasive surgical procedures.

16. The polymeric system of claim 15, wherein the especially modified equipment comprises means for delivering said polymeric system locally in one shot or in a sequential multi-shot manner; wherein said polymeric system may differ in characteristics from shot to shot, and wherein the especially modified equipment comprises means for keeping said polymeric system in a desired position until cross-linking occurs.

17. The responsive polymeric system of claim 1, wherein said solid reinforcing component is of tissular source.

18. The responsive polymeric system of claim 1, wherein said solid reinforcing component is selected from a group consisting of elastin, a collagenous material, albumin, a fibrinous material, demineralized tissue or an acellular tissue matrix and combinations thereof.

19. The responsive polymeric system of claim 1, wherein said solid reinforcing component contains a biomolecule/s, to be delivered into the body.

20. The responsive polymeric system of claim 19, wherein molecule or molecules displaying biological activity, are delivered into the body following a unimodal or multimodal release kinetics.

21. The polymeric system of claim 1, wherein said reinforcing component is chemically or physically bound to a matrix, before and/or during and/or after deployment.

22. The responsive polymeric system of claim 1, wherein at least one of said responsive components segregates over time due to chemical incompatibility and/or due to a polymerization and/or cross-linking reaction.

23. The polymeric system of claim 1, wherein said polymeric component and said reinforcing component initially form a homogeneous macroscopic system and, over time, at least two phases are formed.

24. The polymeric system of claim 1, wherein said reinforcing component serves as scaffold both ex vivo and in vivo.

25. The polymeric system of claim 24, wherein said scaffold can be created ex vivo or in vivo, in the absence of cells or comprising one or more types of cells, or in the absence or presence of additional molecules.

26. The polymeric system of claim 1, wherein said polymeric system can serve as a matrix for the unimodal or multimodal controlled release of biologically active agents, as a sealant, as a coating or lubricant, or as a transient barrier for the prevention of post-surgical adhesions.

27. The component responsive polymeric system of claim 1, wherein said responsive polymeric system also comprises other non-responsive and non-reinforcing materials, organic, inorganic or biological, polymeric or not, that fulfill other chemical, physical, rheological, mechanical or biological roles.

28. The component responsive polymeric system of claim 27, wherein said responsive polymeric system also comprises other non-responsive materials, selected from a group consisting of growth factors, calcium phosphate, tricalcium phosphate or hydroxyapatite, metal magnetic particles, and combinations thereof.

* * * * *